United States Patent [19]

Inamoto et al.

[11] 4,120,906

[45] Oct. 17, 1978

[54] 1-HALOGENOTRICYCLO [4.3.1.1$^{2,5}$] UNDECANE AND PROCESS FOR THE PREPARATION THEREOF

[75] Inventors: Yoshiaki Inamoto; Koji Aigami; Motoyoshi Ohsugi; Hiroshi Ikeda; Yoshiaki Fujikura, all of Wakayama, Japan

[73] Assignee: Kao Soap Co., Ltd., Tokyo, Japan

[21] Appl. No.: 833,679

[22] Filed: Sep. 15, 1977

[30] Foreign Application Priority Data

Oct. 7, 1976 [JP] Japan .................................. 51-120983

[51] Int. Cl.$^2$ ............................................. C07C 17/20
[52] U.S. Cl. ............................. 260/648 C; 260/648 R
[58] Field of Search ....................... 260/648 R, 648 C

[56] References Cited

U.S. PATENT DOCUMENTS

| 3,626,017 | 12/1971 | Moore | 260/648 R |
|---|---|---|---|
| 3,789,089 | 1/1974 | Moore | 260/648 R |
| 3,897,479 | 7/1975 | Inamoto et al. | 260/648 R |

OTHER PUBLICATIONS

Fort, Adamantane: The Chemistry of Diamond Molecules, Marcel Dekker, New York, 1976, pp. 120–121.
Stepanov et al., Chem. Abs., 73, 3518.

*Primary Examiner*—C. Davis
*Attorney, Agent, or Firm*—Blanchard, Flynn, Thiel, Boutell & Tanis

[57] ABSTRACT

1-Halogenotricyclo [4.3.1.1$^{2,5}$] undecanes are prepared by reacting tricyclo [4.3.1.1$^{2,5}$] undecane with bromine or by reacting tricyclo [4.3.1.1$^{2,5}$] undecane-1-ol with thionyl halide. The compounds are useful intermediates for preparing 1-aminotricyclo [4.3.1.1$^{2,5}$] undecane hydrochloride which has antiviral activity.

8 Claims, No Drawings

1-HALOGENOTRICYCLO [4.3.1.1$^{2,5}$] UNDECANE AND PROCESS FOR THE PREPARATION THEREOF

BACKGROUND OF THE INVENTION

1. Field of the Invention

The present invention relates to tricyclo-undecane derivatives and processes for preparing same. More particularly, the present invention relates to 1-halogenotriyclo [4.3.1.1$^{2,5}$] undecanes of formula (I) and processes for the preparation thereof:

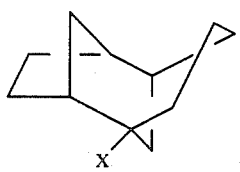

(I)

wherein X is chloro or bromo.

The compounds of the present invention, i.e. 1-halogenotricyclo [4.3.1.1$^{2,5}$] undecane (I), are very useful as intermediates. For example, if a compound of formula (I) of the present invention is reacted with a nitrile, for example, acetonitrile, in the presence of sulfuric acid, the corresponding acyl amino derivative is obtained according to the so-called Ritter reaction. By hydroylsis followed by neutralization of the acyl amino derivative with hydrochloric acid, there can be synthesized 1-aminotricyclo [4.3.1.1$^{2,5}$] undecane hydrochloride which has a strong antiviral activity and is very useful as an ingredient of medicines for human beings.

Tricyclo [4.3.1.1$^{2,5}$] undecane used as the starting material in the present invention is a tricyclo-undecane previously synthesized by the inventors ("J. Chem. Soc.," Perkin Trans. 1, 789 (1975)). After intensive investigations on the functional reactions of the starting compound, the inventors have discovered that the 1-position of the starting compound is selectively brominated by bromine.

1-Bromotricyclo [4.3.1.1$^{2,5}$] undecane, which is one of the compounds of the present invention, can be prepared by direct bromination of tricyclo [4.3.1.1$^{2,5}$] undecane (process A).

Further, 1-halogenotricyclo [4.3.1.1$^{2,5}$] undecane (I) can also be obtained by reacting tricyclo [4.3.1.1$^{2,5}$] undecane-1-ol of formula (II) with a thionyl halide (process B):

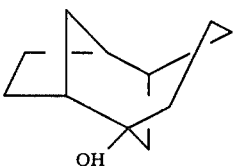

(II)

Tricyclo [4.3.1.1$^{2,5}$] undecane is thus brominated in the 1-position thereof selectively by bromine, in the absence of any catalyst. The fact that the bromination reaction has occurred in the 1-position can be determined with accuracy by measuring the deuterium isotope effects in $^{13}$C NMR spectrum of tricyclo [4.3.1.1$^{2,5}$] undecane containing deuterium.

It is a well-established fact that, in the reactions of polycyclic, cross-linked saturated hydrocarbons, for example, a bromination reaction thereof, wherein a carbonium ion intermediate product of the hydrocarbon is formed, the reaction occurs selectively in a bridgehead position as in the reactions of adamantane, diamantane and 4-homoisotwistane, ("J. Chem. Soc.," Chem. Commun. 371 (1975)). Accordingly, it is considered that also in the starting material of the present invention, i.e. tricyclo [4.3.1.1$^{2,5}$] undecane, the position in which the bromination occurs is the 1- or 2-position (which is similar to the 6- or 5-position, because the molecule has plane-symmetry to a plane including C-8, C-10 and C-11). The position, C-1 or C-2, in which the bromination occurred was determined as described below.

A compound in which C-10 is selectively deuterated (tricyclo [4.3.1.1$^{2,5}$] undecane-10-d$_2$, formula (V)) was synthesized according to the reaction scheme:

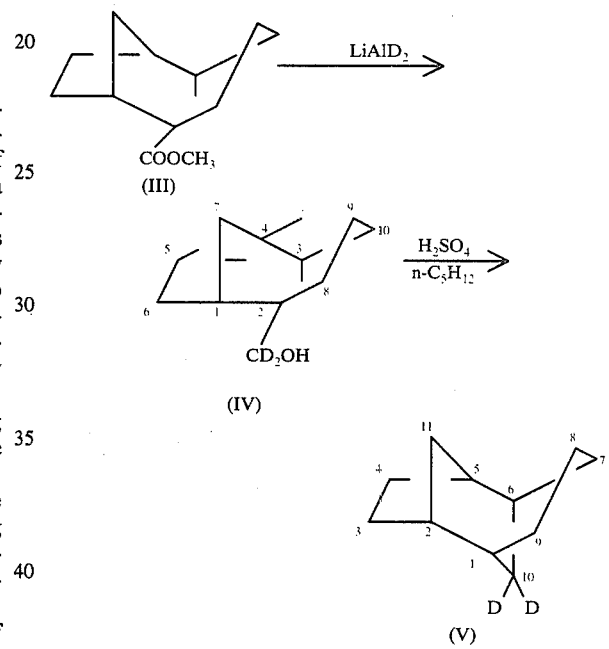

It has been proved already that ring enlargement of endo-2-hydroxymethyl-exo-2,3-trimethylenenorbornane (protium compound corresponding to IV) occurs selectively between the C-2 and C-3 positions (the inventors, "J. Chem. Soc.," Perkin Trans. 1, 789 (1975)). Therefore, it is apparent that the product obtained from deuterium compound (IV) is tricyclo [4.3.1.1$^{2,5}$] undecane-10-d$_2$. (V).

The total proton decoupled $^{13}$C NMR spectrum of tricyclo [4.3.1.1$^{2,5}$] undecane includes seven signals according to C$_s$ symmetry of the molecule. In compound (V), among the seven signals, methylene carbon signal ($\delta$ c 26.41) of a relative strength 1 is split into a quintet fine structure with 0.5 ppm upfield shift by the influence of the two deuterium atoms. Further, only one ($\delta$ c 33.14) of the two methine (bridge head) carbon signals ($\delta$ c 33.14 and 41.16) exhibits an upfield shift of 0.3 ppm with peak broadening. As for the influences of deuterium replacement, the following facts have been recognized, (1) as for the signal of $^{13}$C substituted with deuterium, split into triplet, quintet, . . . is observed depending on the number of deuterium substituents (1,2, . . . ) and, at the same time, an upfield shift is also observed, and (2) carbon (gem-) adjacent to the carbon substituted with deuterium effects a peak broadening and a small (approximately 0.1 ppm) upfield shift (the inventors, "Chem. Lett." 507 (1976) and references cited therein). Accordingly, it is apparent that the thus influenced methylene carbon signal (δ c 26.41) of intensity 1 and the bridge-head carbon signal (δ c 33.14) belong to C-10 and C-1 (and C-6), respectively.

Then, 1-bromotricyclo [4.3.1.1$^{2,5}$] undecane (formula I, X = Br) was reduced with metallic lithium in t-butyl alcohol containing deuterium bound to O (t-BuOD) (the inventors, "Chem. Lett." 507 (1976)) to obtain the corresponding deuterium compound (tricyclo [4.3.1.1$^{2,5}$] undecane-1-d$_1$, formula (VI)).

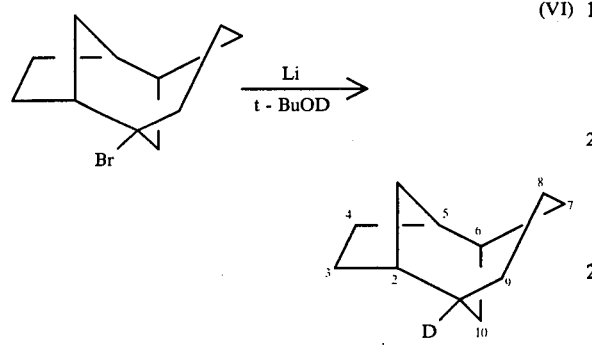

In the $^{13}$C NMR spectrum of compound (VI), it was observed that the signal (δ c 33.14) belonging to C-1 is split into triplet (J-20H$_2$) with 0.9 ppm upfield shift and the other methine (bridgehead) carbon signal (δ c 41.16) and the signal (δ c 26.41) belonging to C-10 as above are influenced as adjacent deuterated carbon atoms.

$^{13}$C NMR signals of C-1 (C-6), C-2 (C-5) and C-10 are thus determined by using deuterium compounds (V) and (VI). From this, it was proved with accuracy that the position of the deuterium substitution in compound (VI) is the 1-position and, accordingly, the position of the bromine substitution in 1-bromotricyclo [4.3.1.1$^{2,5}$] undecane (formula I, X = Br), which is the starting material of (VI), is the 1-position.

Two processes for preparing compounds of formula (I) of the present invention have been found by the inventors. In process A, tricyclo [4.3.1.1$^{2,5}$] undecane is reacted with bromine to obtain 1-bromotricyclo [4.3.1.1$^{2,5}$] undecane. In process B, tricyclo [4.3.1.1$^{2,5}$] undecane-1-ol of formula (II) is reacted with a thionyl halide to obtain 1-halogenotricyclo [4.3.1.1$^{2,5}$] undecane (formula I, X = Br or Cl).

In carrying out process A, no catalyst is required at all. Only the 1-brominated product is obtained selectively, because the stability of the carbonium ion of C-1 (C-6) of tricyclo [4.3.1.1$^{2,5}$] undecane is far higher than that of carbonium ions in other possible positions.

Bromine is used in an amount of 1-20 moles, preferably 3-10 moles, per mole of tricyclo [4.3.1.1$^{2,5}$] undecane. The reaction temperature is in the range of 0° to 58° C., preferably in the range of 10° to 35° C. If the bromination is effected by using bromine in an amount in said range at a reaction temperature in said range, the reaction is completed within 24 hours. Although any of the usual inert organic solvents can be used, it is preferred to carry out the reaction without a solvent from the viewpoint of ease of after-treatment.

Ticyclo [4.3.1.1$^{2,5}$] undecane, used as the starting material in process A, can be obtained easily by, for example, a process found by the inventors wherein endo-1-hydroxymethyl-exo-2,3-trimethyleneorbornane is subjected to hydride transfer reduction rearrangement ("J. Chem. Soc.," Perkin Trans. 1, 789 (1975)) in the presence of sulfuric acid catalyst.

In carrying out process B, the starting material, i.e. tricyclo [4.3.1.1$^{2,5}$] undecane-1-ol, is reacted with a thionyl halide in an aprotic solvent or in the absence of a solvent. The thionyl halide is used in an amount of 1-10 moles, preferably 2-5 moles, per mole of the starting material. The reaction temperature is 0° to 138° C., preferably 79° to 138° C. If the halogenation is carried out under the above reaction conditions, the reaction is completed within three hours. As aprotic solvents which can be used in the present invention, there can be mentioned hydrocarbons such as benzene, toluene and hexane and halogenated hydrocarbons such as carbon tetrachloride and chloroform.

Tricyclo [4.3.1.1$^{2,5}$] undecane-1-ol used as the starting material in process B can be obtained easily by, for example, an isomerization reaction developed by the inventors wherein endo-2-hydroxymethyl-exo-2, 3-trimethylene norbornane is isomerized in the presence of sulfuric acid catalyst. This endo-2-hydroxymethyl-exo-2, 3-trimethylenenorbornane can be obtained easily by reducing a carboxylic acid obtained by reacting exo-5-hydroxy-exo-2, 3-trimethylene-norbornane or exo-2,3-trimethylene-5-norbornene with formic acid or carbon monoxide in sulfuric acid according to a method of Koch, et al. (Koch, et al., "Ann." 638, 111 (1960) (the inventors "J. Chem. Soc." Perkin Trans. 1, 789 (1975)).

The present invention will be further described in the following illustrative examples. A process for preparing tricyclo [4.3.1.1$^{2,5}$] undecane-1-ol used as the starting material of process B is also shown as a preparation.

EXAMPLE 1

Preparation of 1-bromo-tricyclo [4.3.1.1$^{2,5}$] undecane (process A):

1.0 Gram (4.8 millimoles) of tricyclo [4.3.1.1$^{2,5}$] undecane is added to 2 ml (38.7 millimoles) of liquid bromine and the entirety is stirred at room temperature for 17 hours. The reaction mixture is added slowly to a cooled, saturated solution of sodium hydrogensulfite under stirring to decompose excess bromine. The aqueous solution is subjected to two extractions each with 20 ml of carbon tetrachloride and the combined extracts are dried with magnesium sulfate. Carbon tetrachloride is distilled out and the residue (1.9 g) is distilled under reduced pressure to collect a fraction boiling at 96°-8° C./2mmHg. Colorless crystals having a melting point of 57.5°-58.5° C. are thus obtained.

Elementary analysis:
Found: — C, 57.2; H, 7.4; Br, 34.2%
Calculated (C$_{11}$H$_{17}$Br):
C, 57.7; H, 7.5; Br, 34.9%

IR (Nujol, cm$^{-1}$)
3030, 1295, 1240, 1155, 1060, 1000, 995, 960, 760

$^1$H NMR (CDCl$_3$ solvent, TMS internal standard, δ)
0.8–2.8 (multiplet)

$^{13}$C NMR (CDCl$_3$ solvent, TMS internal standard, δc)
22.46(t), 26.52(t), 27.98(t and t), 34.27(t), 37.77(d), 39.35(t), 39.80(d), 41.18(t), 51.41(d), 75.08(s)

Mass spectrum m/e (relative intensity):
230(0.1,M$^+$), 228(0.2,M$^+$), 150(13), 149(100), 107(15), 91(15), 83(18), 81(44), 79(23), 67(8).

EXAMPLE 2 (Process B)

Six milliliters (78 millimoles) of thionyl bromide are added to 20 ml of a solution of 5.36 g (32 millimoles) of tricyclo [4.3.1.1$^{2,5}$] undecane-1-ol in dry benzene and the entirety is refluxed for 1.5 hours. The reaction mixture is concentrated under reduced pressure and there is further added 20 ml of dry benzene. Reduced pressure concentration is repeated to distill out the excess thionyl chloride completely. The residue is distilled under reduced pressure to collect a fraction boiling at 96°-8° C./2mmHg. Thus 4.53 g (yield 61.3%) of 1-bromotricyclo [4.3.1.1$^{2,5}$] undecane are obtained. After cooling, colorless crystals having a melting point of 57.7°-58.5° C. are obtained. The properties of this product are the same as those shown in Example 1.

EXAMPLE 3 (Process B)

Five milliliters of thionyl chloride are added to a solution of 5.0 g (30 millimoles) tricyclo [4.3.1.1$^{2,5}$] undecane-1-ol in 30 ml dry anhydrous benzene and the entirety is refluxed for 1.5 hours. The reaction mixture is concentrated under reduced pressure and there is further added 20 ml of dry benzene. Reduced pressure concentration is repeated to distill out the excess thionyl chloride completely. The residue is distilled under reduced pressure to collect a fraction boiling at 95° C./3mmHg, to obtain 5.0 g (yield 89%) of 1-chlorotricyclo [4.3.1.1$^{2,5}$] undecane.

Melting point 68°-69° C.

Elementary analysis:

Found: — C, 71.3; H, 9.0; Cl, 19.7%

Calculated (as $C_{11}H_{17}Cl$):

C, 71.5; H, 9.2; Cl, 19.3%

IR (KBr, cm$^{-1}$)

3030, 2940, 2880, 1485, 1470, 1000, 880, 765

Mass spectrum m/e (relative intensity):

186 (4,M$^+$), 184 (12,M$^+$), 150 (12), 149 (100), 141 (10), 135 (11), 115 (18), 113 (11), 93 (14)

PREPARATION

A solution of 40 g (0.24 mole) of endo-2-hydroxymethyl-exo-2,3-trimethylenenorbornane (III) in 100 ml of carbon tetrachloride is added to 400 ml of cooled 50% aqueous sulfuric acid solution. After stirring the entirety at room temperature for 35 hours, the reaction mixture is extracted three times, each time with 200 ml of diethyl ether. The extract is washed with saturated sodium hydrogencarbonate sodlution and then with water. The ether solution is dried with anhydrous sodium sulfate. Ether is distilled out. After purification by sublimation, 39.2 g (yield 98%) of tricyclo [4.3.1.1$^{2,5}$] undecane-1-ol are obtained.

Elementary analysis (%):

Found — C, 79.4; H, 10.6

Calculated (as $C_{11}H_{18}O$):

C, 79.52; H, 10.84

IR (Nujol, cm$^-$):

3280, 3030, 1480, 1465, 1340, 1090, 1075, 1035, 945

Mass spectrum m/e (relative intensity)

166 (0.3, M$^+$), 123 (57), 98 (7), 97 (100), 95 (23), 81 (5), 79 (9), 77 (5)

The embodiments of the invention in which an exclusive property or privilege is claimed are defined as follows:

1. 1-Halogenotricyclo [4.3.1.1$^{2,5}$] undecane having the formula (I):

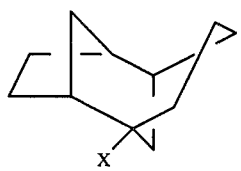

wherein X is chloro or bromo.

2. A process for preparing 1-bromotricyclo [4.3.1.1$^{2,5}$] undecane which comprises reacting tricyclo [4.3.1.1$^{2,5}$] undecane with bromine.

3. A process for preparing 1-bromotricyclo [4.3.1.1$^{2,5}$] undecane according to claim 2 in which from one to 20 moles of bromine are used per mole of tricyclo [4.3.1.1$^{2,5}$] undecane.

4. A process for preparing 1-bromotricyclo [4.3.1.1$^{2,5}$] undecane according to claim 2 in which the reaction temperature is in the range of 0° to 58° C.

5. A process for preparing 1-bromotricyclo [4.3.1.1$^{2,5}$] undecane according to claim 2 in which the reaction is carried out in the absence of a solvent.

6. A process for preparing 1-halogenotricyclo [4.3.1.1$^{2,5}$] undecane which comprises reacting tricyclo [4.3.1.1$^{2,5}$] undecane-1-ol of formula (II) with a thionyl halide wherein the halogen is bromine or chlorine;

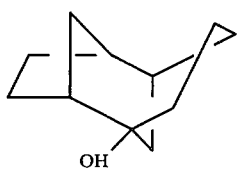

7. A process for preparing 1-halogenotricyclo [4.3.1.1$^{2,5}$] undecane according to claim 6 wherein from one to 10 moles of thionyl halide is reacted per mole of tricyclo [4.3.1.1$^{2,5}$] undecane-1-ol.

8. A process for preparing 1-halogenotricyclo [4.3.1.1$^{2,5}$] undecane according to claim 7 wherein the reaction is carried out in an aprotic solvent or in the absence of a solvent at a reaction temperature in the range of 0° to 138° C.

* * * * *